United States Patent
Virta et al.

(10) Patent No.: US 7,085,346 B1
(45) Date of Patent: Aug. 1, 2006

(54) ARRANGEMENT AND METHOD FOR MEANS FOR RECEIVING IMAGE DATA IN MAMMOGRAPHY

(75) Inventors: Arto Virta, Helsinki (FI); Pekka Strömmer, Espoo (FI); Timo Sulin-Saaristo, Helsinki (FI)

(73) Assignee: Planmed Oy, Helsinki (FI)

( * ) Notice: Subject to any disclaimer, the term of this patent is extended or adjusted under 35 U.S.C. 154(b) by 0 days.

(21) Appl. No.: 10/130,868

(22) PCT Filed: Nov. 24, 2000

(86) PCT No.: PCT/FI00/01030

§ 371 (c)(1),
(2), (4) Date: May 22, 2002

(87) PCT Pub. No.: WO01/38938

PCT Pub. Date: May 31, 2001

(30) Foreign Application Priority Data

Nov. 26, 1999 (FI) .................................. 19992538

(51) Int. Cl.
*A61B 6/04* (2006.01)
(52) U.S. Cl. .............................. 378/37; 378/172
(58) Field of Classification Search ............... 378/37, 378/165, 166, 169, 176, 175, 172–174, 162, 378/170, 167; 250/589, 581
See application file for complete search history.

(56) References Cited

U.S. PATENT DOCUMENTS

| | | | | |
|---|---|---|---|---|
| 3,743,843 A | * | 7/1973 | Reser et al. | 378/27 |
| 3,826,922 A | * | 7/1974 | Ingles | 378/181 |
| 4,249,079 A | * | 2/1981 | Thomas | 378/176 |
| 4,845,733 A | * | 7/1989 | Dieterlen et al. | 378/177 |
| 4,983,991 A | | 1/1991 | Palonen | 346/33 |
| 4,989,227 A | * | 1/1991 | Tirelli et al. | 378/177 |
| 5,081,357 A | * | 1/1992 | Agano | 250/589 |
| 5,148,466 A | * | 9/1992 | Fajac | 378/167 |
| 5,333,170 A | | 7/1994 | Blasi | 378/166 |
| 5,539,797 A | | 7/1996 | Heidsieck et al. | 378/37 |

FOREIGN PATENT DOCUMENTS

| | | |
|---|---|---|
| DE | 3022248 | 12/1981 |
| DE | 4140718 | 6/1992 |
| EP | 0775467 | 6/1997 |

* cited by examiner

*Primary Examiner*—Edward J. Glick
*Assistant Examiner*—Hoon Song
(74) *Attorney, Agent, or Firm*—Wolf Block Schorr & Solis-Cohen, LLP

(57) ABSTRACT

The imaging apparatus used in mammography generally having a cassette tunnel (17) or a similar space for the placement of an image data receiving device (14') in the imaging area of the apparatus. In such a space or in its immediate vicinity, device (19) for moving the cassette in the space can be provided, thus making the imaging process in many ways faster and easier to carry out. Such device for moving the cassette can also be utilized in various ways to achieve a more versatile and more accurate use of the imaging apparatus.

44 Claims, 4 Drawing Sheets

ARRANGEMENT AND METHOD FOR MEANS FOR RECEIVING IMAGE DATA IN MAMMOGRAPHY

FIELD OF THE INVENTION

The present invention relates to an arrangement for image data receiving means, such as a film cassette or equivalent for use in mammography and to a method for image data receiving means used in mammography and to a mammography apparatus in which the image data receiving means can be used. In particular, the invention concerns solutions regarding the loading, removal and movement of the image data receiving means in the cassette tunnel or similar space of mammography apparatus.

BACKGROUND OF THE INVENTION

The image data receiving means generally used in mammography are x-ray films placed in cassettes. Such cassettes are available in several different types, depending e.g. on the manufacturer of the cassette and the type of imaging the cassette is designed for. Often there are also differences between cassettes according to whether the film used in them is intended to be developed in a darkroom or e.g. in a special film development device. These so-called daylight cassettes are gradually replacing darkroom cassettes. In this field, many kinds of devices for the loading of cassettes with a film and for the removal of the film from cassettes have been developed, and likewise different labeling devices, i.e. devices e.g. for printing or exposing patient information and imaging parameters on the film in a cassette.

The imaging apparatus used in mammography generally have in their imaging area a space with at least one feed/eject opening, a cassette tunnel or equivalent, into which a cassette loaded with a film is entered and where it is positioned at a desired imaging position and from where it is removed and taken to a separate labeling stage. In many imaging apparatus, the cassette tunnel is so implemented that its open end or ends form a cassette feed/eject opening. When both ends of the tunnel are open, the cassette can be moved in the tunnel by pushing it from one end of the tunnel and pulling from the other. Moreover, in some devices the tunnel wall is provided with additional holes to make it easier to move the cassette.

However, handling the cassette in such a cramped tunnel, besides being difficult and awkward, is also time-consuming. Especially in mammographic screening studies, in which the cassette may have to be changed as many as 50 times an hour, cassette handling alone takes up a considerable amount of time, and for an individual patient this means that the imaging operation, which many patients find unpleasant, takes an annoyingly long time.

Traditionally, mammography apparatus have been used to take various individual transillumination radiographs. However, the information given by a transillumination radiograph is not always sufficient in a diagnostic sense. For this reason, there has been a trend in recent times towards discovering new imaging methods e.g. to make different layers in the tissue under imaging more clearly visible in the images. A contribution to this development has been the progress in the technology and prices of digital sensors toward a level that is beginning to enable their use in mammography apparatus, too, both in an economic sense and in respect of image quality and authority approval.

In many imaging modes that are more complex than transillumination imaging, a requirement is that it should be possible to change in some way the position of the object to be imaged with respect to the imaging means during the imaging process. Such a change can be implemented either as a stepwise action or as a continuous movement during imaging. When controlled movement of the object to be imaged is difficult to achieve, as is the case in mammography, one can naturally seek for means for moving the imaging means.

Prior-art mammography apparatus have means for moving the imaging means in relation to the object to be imaged e.g. to change the height position of the imaging means in relation to the object to be imaged, means for interdependently revolving the imaging means around the object to be imaged, and means for inclining the radiation source in relation to the object to be imaged and the image data receiving means. As for other movements, certain apparatus also have means for moving e.g. a screen placed near the radiation source to define the radiation beam in a desired manner, and even means for moving the object to be imaged during the imaging process. However, independent movements of image data receiving means that may be needed during imaging have been difficult to implement in a desired manner because, if the structure of the apparatus has permitted such movements at all, they have had to be carried out manually.

In some mammography apparatus, difficulties have been encountered in getting the cassette correctly positioned in the imaging area. If the cassette is in the wrong position, this may result in leaving part of the tissue to be imaged outside the area of which an image is formed on the film or other receiving medium, which may necessitate renewal imaging. This creates extra work and an unnecessary additional exposure of the tissue to radiation.

Often the actions requiring handling of the cassette in the cassette tunnel have to be performed in ergonomically difficult working positions. This is the case especially when more than one image is taken of the same object, possibly even on the same film, in which case the cassette has to be changed or moved to a new position in the cramped cassette tunnel while the object to be imaged may remain positioned during all this time, in mammography in practice generally compressed between the compression plates of the imaging apparatus.

Recording patient information, dates, imaging parameters and projections etc. on the film or equivalent is an essential part of the imaging process. Especially in mammographic screening studies referred to above, there is a great risk of labeling errors occurring due to human factors. When the actions related to labeling are carried out as an operation physically separate from the actual imaging process, the cassettes may be interchanged when being taken from the imaging apparatus to the labeling station. Thus, information of a wrong patient and/or wrong imaging parameters may be entered on the film. And when human activities are concerned, it may even happen that some or even all of the data is not recorded at all when the labeling of an individual cassette or a whole batch of cassettes is accidentally neglected e.g. as a result of a lapse of memory. On the whole, labeling the films is an operation that requires accurate management and contributes for its part to the total duration of the imaging process.

OBJECTS AND SUMMARY OF THE INVENTION

The object of the invention is to eliminate above-mentioned drawbacks in a profitable way that improves working comfort and ergonomics in the imaging process, which involves no need to enter or remove the film cassette through narrow holes or to move it in the cramped cassette tunnel of the mammography apparatus.

One of the objects of the invention is to enable a more efficient utilization of time especially in conjunction with mammographic screening studies by reducing the time spent between exposures.

A further object of the invention is to achieve an arrangement in which, when a cassette is being loaded into the mammography apparatus, an automatic system according to preferred embodiments of the invention seizes the cassette and drives it to the correct imaging position in the cassette tunnel, thus allowing the operator of the apparatus to proceed sooner to other actions in preparation for imaging.

A further object of the invention is to enable accurately correct positioning of the image data receiving means in the imaging area so as to minimize the need for taking renewed images in consequence of inaccurate positioning of the tissue to be imaged.

Another object of the invention is to achieve an arrangement in which an exposed cassette can be automatically driven out of the cassette tunnel when desired, so that the operator of the apparatus could easily change/remove the cassette without having to dig it out from the opening of the cassette tunnel.

In certain preferred embodiments of the invention, the object is to achieve an arrangement in which the recording of patient information and imaging parameters on the film, which constitutes an essential part of the imaging process, can be performed automatically in the imaging apparatus in connection with the imaging process.

An object of preferred embodiments of the invention is also to achieve an arrangement that can be used for moving image data receiving means of different types and sizes in the imaging area of the imaging apparatus.

A further object of the invention and some of its embodiments is to provide possibilities to use a mammography apparatus even in imaging processes requiring complex movements of the imaging means and their accurate control, and in general to provide better possibilities to accurately and with ease move the imaging means in mammographic imaging processes.

The problems described above are solved and the objects stated are achieved by a solution according to the fundamental idea of the invention disclosed in the present application, in which the mammography apparatus is provided with devices by means of which the image data receiving means can be easily and accurately moved in the cassette tunnel or a corresponding space in the mammography apparatus, using control means and/or automatically.

In the following, some of the preferred embodiments of the invention will be described in greater detail with reference to the attached drawings. However, the invention is not intended to be exclusively limited to these embodiments; instead, its exact essential features are presented in the claims below. In the attached drawings,

BRIEF DESCRIPTION OF THE DRAWINGS

In the following, some of the preferred embodiments of the invention will be described in greater detail with reference to the attached drawings. However, the invention is not intended to be exclusively limited to these embodiments; instead, its exact essential features are presented in the claims below. In the attached drawings.

DETAILED DESCRIPTION OF THE INVENTION

Figure 1:
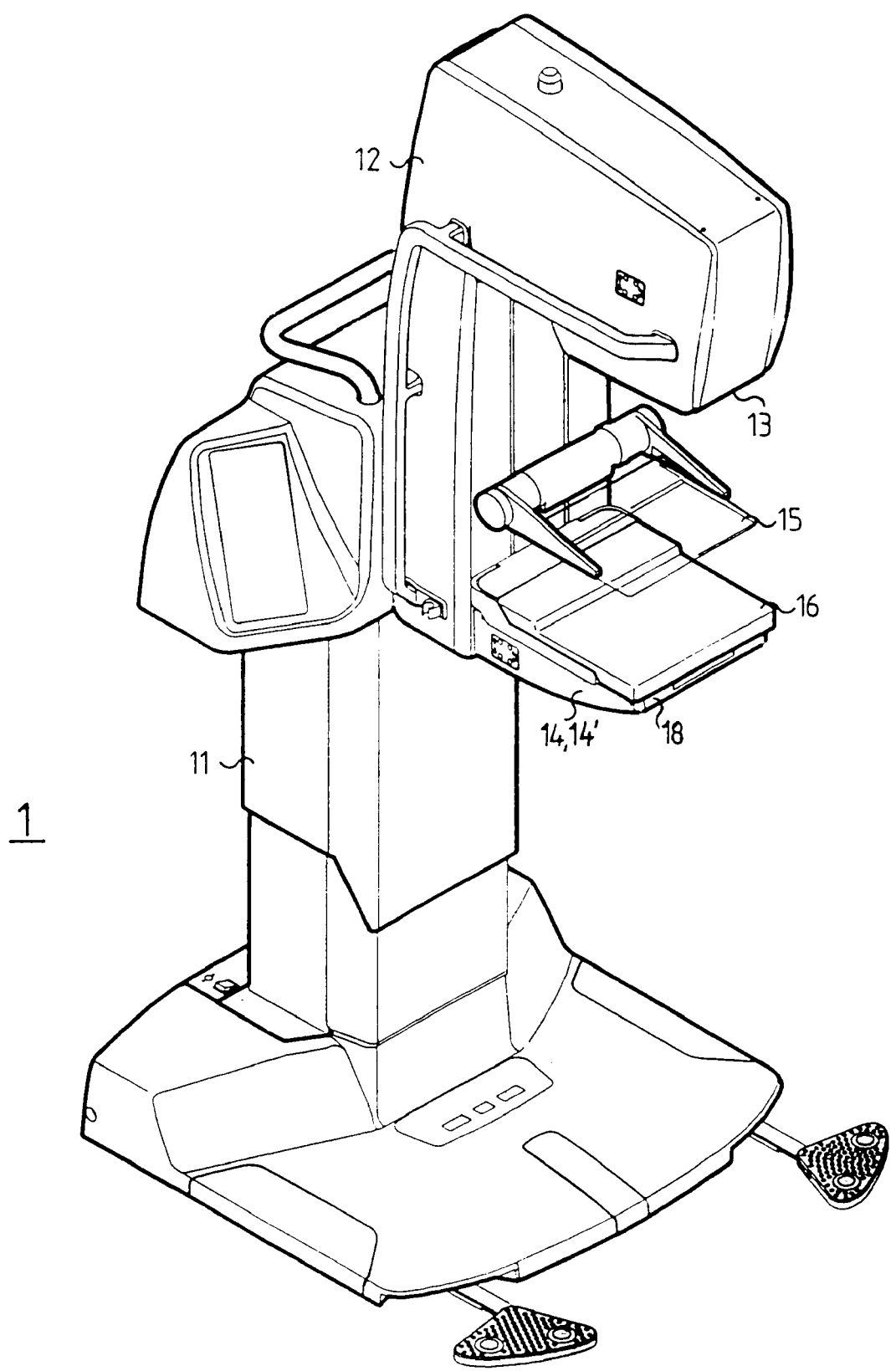
FIG. 1 presents a typical mammography x-ray apparatus.

The mammography x-ray apparatus 1 presented in FIG. 1 consists of a frame part 11 and a C-arm 12 connected to it. Typically, placed at opposite ends of the C-arm 12 are a radiation source 13 and an image data receiving means 14', which is located e.g. inside a so-called bottom shelf structure 14. These imaging means 13, 14', being placed inside the casing of the apparatus, are not actually visible in FIG. 1. In addition, placed in the area between these imaging means 13, 14', typically near the image data receiving means 14', are means 15, 16 for positioning the object to be imaged in the imaging area. Typically, the C-arm 12 can be both moved vertically and horizontally in relation to the means 15, 16 for positioning the object to be imaged and rotated in relation to the frame part 11. The positioning means 15, 16 typically consist of an upper compression plate 15 and a lower compression plate 16, and the lower compression plate 16 may also be arranged to function as a so-called bucky. "Bucky" means a grid structure placed between the tissue to be imaged and the image data receiving means to prevent radiation scattered from the tissue from reaching the image data receiving means.

Figure 2:
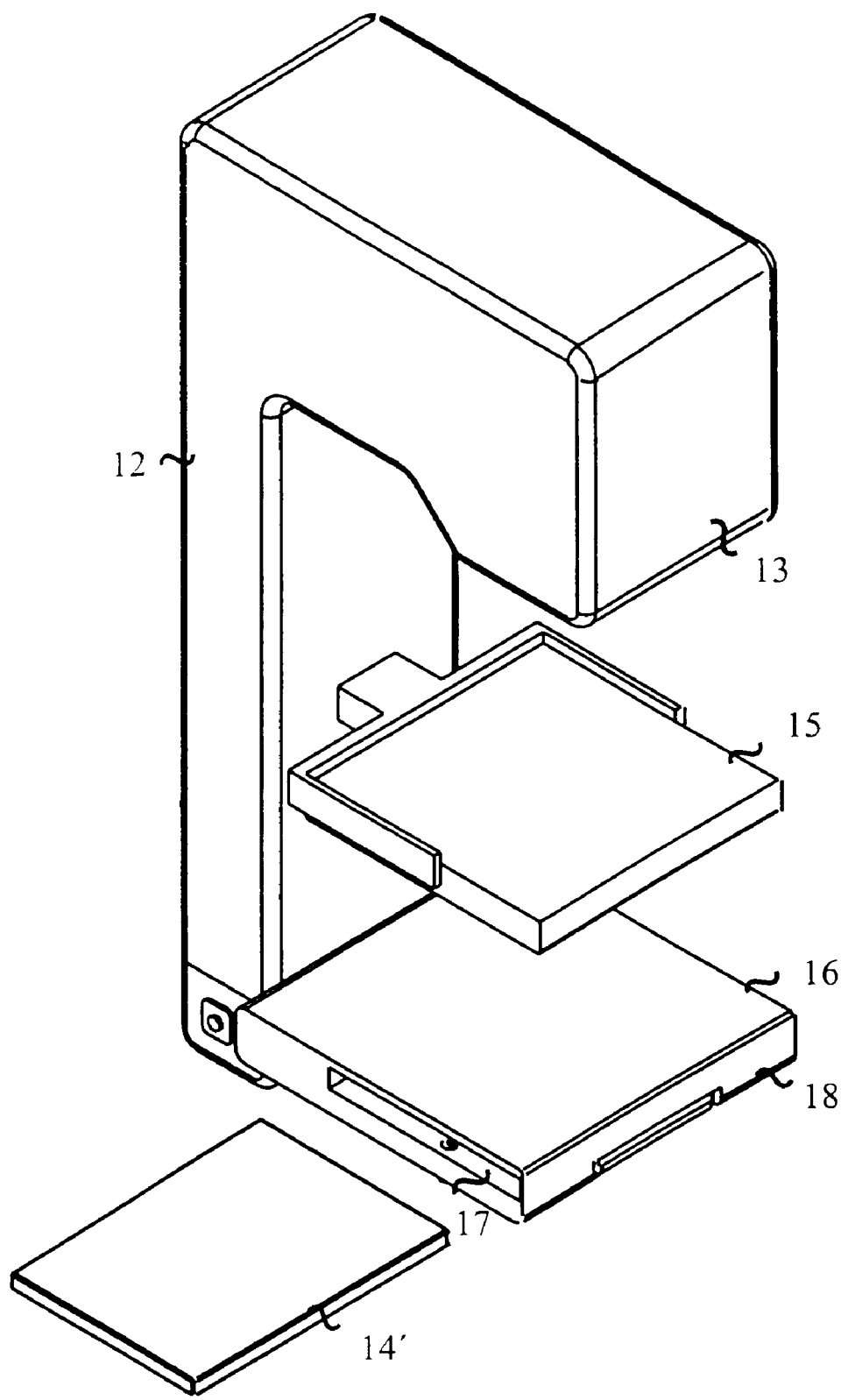
FIG. 2 presents a typical C-arm structure of the mammography apparatus.

FIG. 2 presents one C-arm structure 12 used in mammography apparatus. The C-arm 12 in FIG. 2 differs from the structure in FIG. 1 especially in respect of the way in which the cassette tunnel or similar space 17 has been arranged in the imaging area of the apparatus. The solution illustrated in FIG. 1, in which both ends of the cassette tunnel 17 are closed and a cassette 14' is entered into the cassette tunnel 17 by driving the bottom shelf structure 14 downwards so that a space is formed between it and the lower compression plate 16, allowing the cassette 14' to be inserted into the cassette tunnel 17 via this space from above, is fairly seldom used in mammography apparatus. FIG. 2 presents perhaps a more typical solution, in which at least one end of the cassette tunnel 17 is open, allowing the cassette 14' to be inserted directly into the tunnel 17 from the side of the structure, without requiring operation of the means for driving the C-arm 12.

Generally speaking, in mammography systems there are used more or less integrated structures of several different types for forming the assembly consisting of the bottom shelf, lower compression plate and bucky/grid 14, 16 and the associated cassette tunnel or similar space 17. For example, in the solution illustrated in FIG. 2, the cassette tunnel 17 has been integrated as a part of the lower compression plate/bucky/grid structure 16 of the apparatus. Anyway, all cassette tunnel solutions have the common aim of bringing one edge of the cassette tunnel 17 as close as possible to that wall 18 of the bottom shelf or similar structure 14, 16 which comes into contact with the chest during imaging, because the image data receiving means must be so placed in the imaging area as to allow a maximal amount of tissue even in the region of the sternum and armpit to be imaged.

When the cassette tunnel 17 has been arranged to be loaded in a horizontal plane—while the C-arm 12 of the mammography apparatus is in a vertical position as shown in FIG. 2, its feed/eject opening is generally disposed in a lateral location as seen from the direction 18 from which the tissue to be imaged is entered. This obviates the need for re-positioning the object to be imaged, which is an awkward operation that may be unpleasant to the person being imaged, only because a change of cassette 14' is needed.

Figure 3:
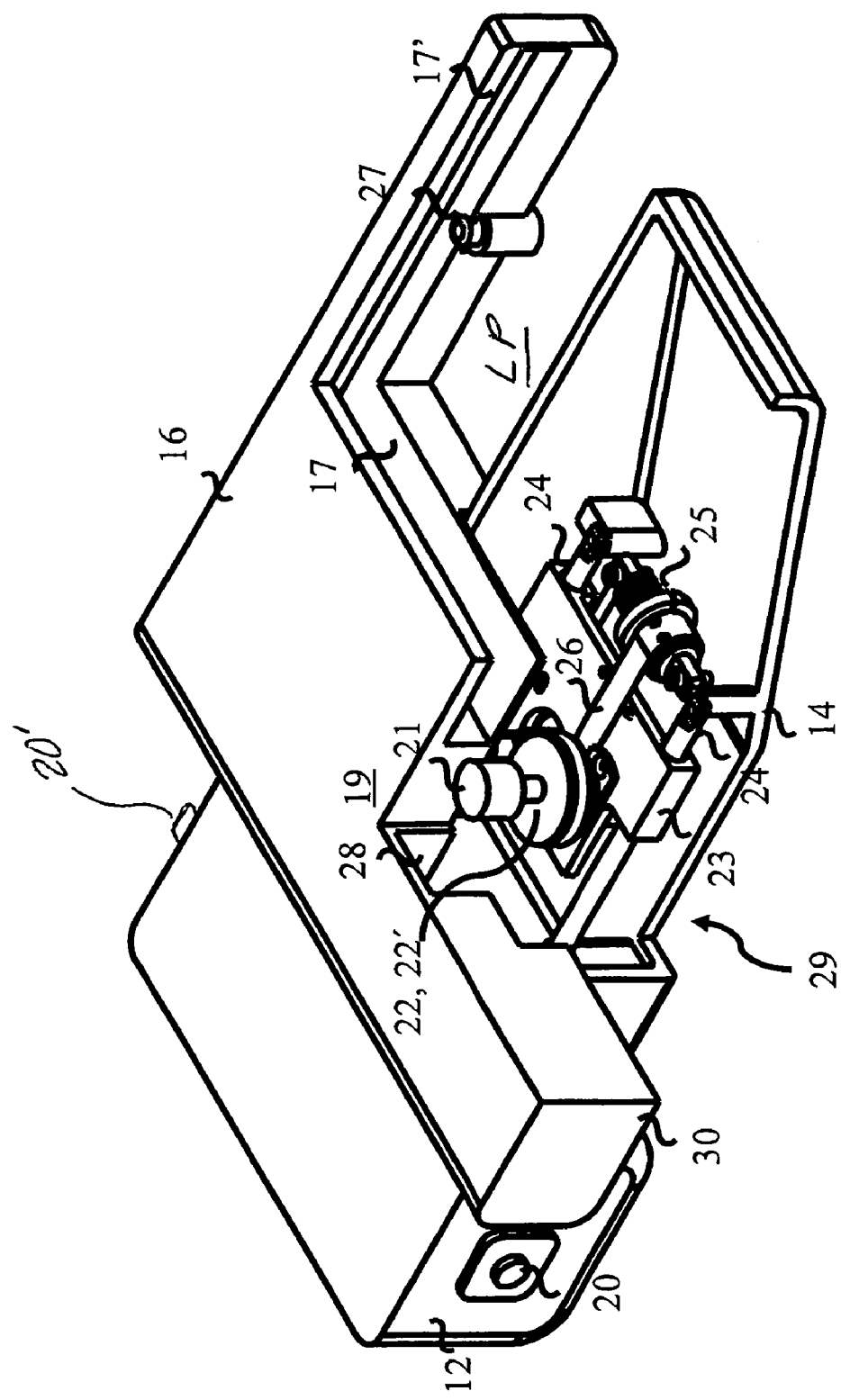
FIG. 3 presents an arrangement according to the invention for moving the image data receiving means that are used in mammography.

FIG. 3 illustrates an arrangement according to the invention which allows the entry, the ejection and if so desired, even other kinds of movements of a film cassette 14' in the cassette tunnel 17. In the embodiment illustrated in FIG. 3, the arrangement for moving the cassette 14' in the cassette tunnel 17 comprises a bottom shelf 14, depicted in a sectioned view in the figure, means 19 for moving the cassette 14', a button 20 for starting the ejection of the cassette 14', and a bucky 16. The means 19 for moving the cassette 14' comprise a driving roller 21, a driving roller motor not visible in the figure, being placed below the bottom shelf 14, and a turning shaft 22 functionally connecting the roller 21 and its motor and provided with a gearing 22'. In the arrangement in FIG. 3, the cassette tunnel 17 is so implemented that it forms a part of the bucky 16, with an opening/openings 17' at its sides serving as cassette 14' feed/eject openings. The means 19 for moving the cassette 14' are mounted on a carriage 23 which can be moved along guide rails 24 and which is connected to a spring 25 continuously tending to draw it by means of a drawing band 26 toward that end 18 of the bucky 16 which comes into contact with the chest. The bottom of the bottom shelf 14 is also provided with an elongated aperture 29, shown in FIG. 3, laid in a direction parallel to the guide rails 24, the shaft 22 of the driving roller 21 going through this aperture. Thus, the means 19 for moving the cassette 14' can move in the direction of this aperture and the guide rails 24. The cassette tunnel 17, e.g. its bottom, may additionally be provided with one or more sensors 27 which are connected to the control means 30 of the apparatus to probe the position of the cassette 14' in the cassette tunnel 17.

Disposed on the side opposite to that wall 18 of the bucky 16 that comes into contact with the chest of the object to be imaged is arranged an elongated cut-out or groove 28 substantially parallel to the guide rails 24, into which the shaft of the driving roller 21 is directed when the bucky 16 is being mounted on the bottom shelf 14 from the direction of the wall 18 placed against the chest. The length of this cut-out 28 is so designed that it will position the driving roller 21 in relation to the cassette tunnel 17 so that the circumference of the roller 21 will come into contact with the side wall of the cassette 14' as it is fed in the cassette tunnel 17. A spring 25 continuously draws the means 19 for moving the cassette 14' toward the cassette 14', ensuring that a frictional force sufficient for converting the rotational motion of the roller 21 into a linear movement of the cassette 14' exists between the sidewall of the cassette 14' and the driving roller 21. In the solution illustrated in FIG. 3, the guide slot 28 and guide rails 24 for guiding the bucky 16 are disposed at an angle substantially perpendicular to the feed direction of the cassette 14' in the cassette tunnel 17, but naturally they may also be arranged at a different angle.

In mammography, cassettes 14' of different sizes are commonly used to meet different imaging needs. The arrangement presented in FIG. 3 is modified so as to allow the use of another cassette size, by replacing the bucky 16 on the bottom shelf 14 with one having a cassette tunnel 17 dimensioned for the other cassette size and a cut-out or recess 28 coming into contact with the driving roller 21 that has a length corresponding to this arrangement, by means of which cut-out or recess the means 19 for moving the cassette 14' are moved along the guide rails 24 to correct position for moving this different-sized cassette 14'.

The arrangement illustrated in FIG. 3 may function e.g. as follows. When a cassette 14' is fed through the feed opening 17' into the cassette tunnel 17, the control system 30 of the apparatus detects by means of a sensor 27 placed in the tunnel 17 that a cassette 14' has been entered in the tunnel 17 and starts the drive motor of the driving roller 21. As the cassette 14' is pushed further in, its rear edge meets the driving roller 21, which begins to draw the cassette 14' into the tunnel 17, whereupon the person inserting the cassette 14' can release his/her grip of it. Preferably, into the cassette tunnel 17 open at both of its ends a sensor 27 is provided in the area of both of the feed openings, in which case the control system 30 will control the drive motor of the driving roller 21 to rotate in the appropriate direction to draw the cassette 14' into the tunnel.

Disposed at a suitable location at the other end relative to the feed opening 17' of the tunnel 17, there may be another sensor (not shown in the figure) to detect the edge of the cassette 14', allowing the control system either to stop the motor or to drive the cassette 14' from this detection point to a given other imaging position as required in each case. In most cases, this position is the location where the midpoint of the cassette 14' lies on the center axis of the field of rays used for imaging. According to the invention, the control system of the apparatus may be so implemented that it also includes an ability to measure and learn the correct position of the cassette 14' in the tunnel 17. After the cassette 14' has been correctly positioned, the control system gives a permission for starting the actual imaging process.

Upon completion of the imaging process, the means 19 for moving the cassette 14' drive the cassette 14' out of the cassette tunnel 17 either on the basis of a signal obtained from a cassette eject button 20 or automatically e.g. via a predetermined eject opening. The arrangement preferably comprises two or an even number of cassette eject buttons 20, 20', which are disposed substantially near each end opening of the cassette tunnel 17. The control system identifies which one of the buttons 20, 20' has been pressed and drives the cassette 14' out of the tunnel 17 via the eject opening corresponding to this button 20, 20'. In the embodiment illustrated in FIG. 3, the means 19 for moving the cassette 14' do not automatically drive the cassette 14' far enough out of the eject opening to allow it to fall but only far enough to make it easy for the operator of the apparatus to get hold of the cassette 14' in order to remove it from the tunnel 17.

Among the advantages of the embodiment of the invention as presented in FIG. 3 are the profitableness resulting from its structural simplicity, and especially its small space requirement. In a mammography apparatus, it is not recommendable to fit any complex arrangements in the regions below the lower compression plate because any large structures in these areas are a significant obstruction to patient positioning for different projections.

In the embodiment presented in FIG. 3, the means for moving the cassette in the cassette tunnel comprise only one roller, but naturally more rollers can be used without departing from the basic idea of the invention.

An alternative solution for providing the apparatus with means for moving the cassette according to the invention is to use two driving rollers immovable in the plane of the cassette feed direction, at least one of which is provided with means for implementing an axial motion of the roller. By placing such cassette moving means at suitable locations in the cassette tunnel or its immediate vicinity, it will be possible to use one driving roller for moving a cassette of one size and another roller for moving a cassette of another size, and this axial movement permits a roller which is used for moving a cassette of a given size but which would prevent some other bucky, cassette and so on from being fed into the cassette tunnel 17 to be drawn out of the cassette tunnel when necessary.

Another alternative way of providing the apparatus with means for moving cassettes of different sizes is to use a single driving roller having an increased length in the direction of its rotation axis, which is brought into the cassette tunnel or to a substantially close vicinity to it in a horizontal position, i.e. in an orientation parallel to the bottom/top of the cassette tunnel, and positioned there in a fixed location. When the length of the roller is suitably selected, it will be long enough to move cassettes of different sizes.

Naturally, a roller is not the only driving means applicable for moving a cassette in the cassette tunnel as provided by the invention; instead, in principle, any known/applicable power transmission solution can be used. However, according to the fundamental idea of the invention, it is preferable to use means that require only little space and that can simply be placed in the cassette tunnel or in its immediate vicinity in a mammography apparatus. Such solutions typically include, however, rollers or other drive wheels or equivalent coming into a direct or indirect contact with the cassette like those described above, from which it is possible to construct simple overall solutions that enable cassettes of different sizes to be moved in the cassette tunnel. Corresponding means can advantageously even be used to provide the cassette tunnel or similar space with a drive system by means of which the cassette can be moved in the tunnel both in its feed direction and in a direction substantially perpendicular to the feed direction. In this way, conditions are created for the use of the imaging apparatus in so-called spiral or complex motion tomographic imaging, or conditions for solutions that can be utilized in one preferred embodiment of the invention, the use of means for moving the cassette in co-action with means for labeling of films, also disposed in the cassette tunnel. In the following, these embodiments of the invention will be described in some more detail, but as for bidirectional cassette movement mentioned above, we can already state at this point that, by suitably arranging the cassette tunnel and the means for moving the cassettes, it will be possible to use in the imaging apparatus even cassettes of different types and sizes whose so-called labeling window may be located at different positions, because, using cassette moving means like this, the cassettes can be correctly positioned in the cassette tunnel in alignment with the labeling device even if the latter are stationarily mounted in the apparatus.

An additional feature of the invention is a possibility to use the cassette moving means even for other purposes besides cassette feed and eject functions and positioning of the cassette in the cassette tunnel. One embodiment of this type relates to the labeling of films, i.e. to the recording of imaging parameters, patient information etc. on the film. FI patent application 19992537 filed simultaneously with the present application contains a more detailed discussion of the problems associated with prior-art labeling arrangements and the special features of an invention concerning a labeling arrangement, presented in the application in question. In this context, we shall only describe an embodiment in which a labeling device as presented in FIG. 4 is so arranged in conjunction with the cassette tunnel as to allow the labeling of the film to be performed directly in the cassette tunnel.

Figure 4:
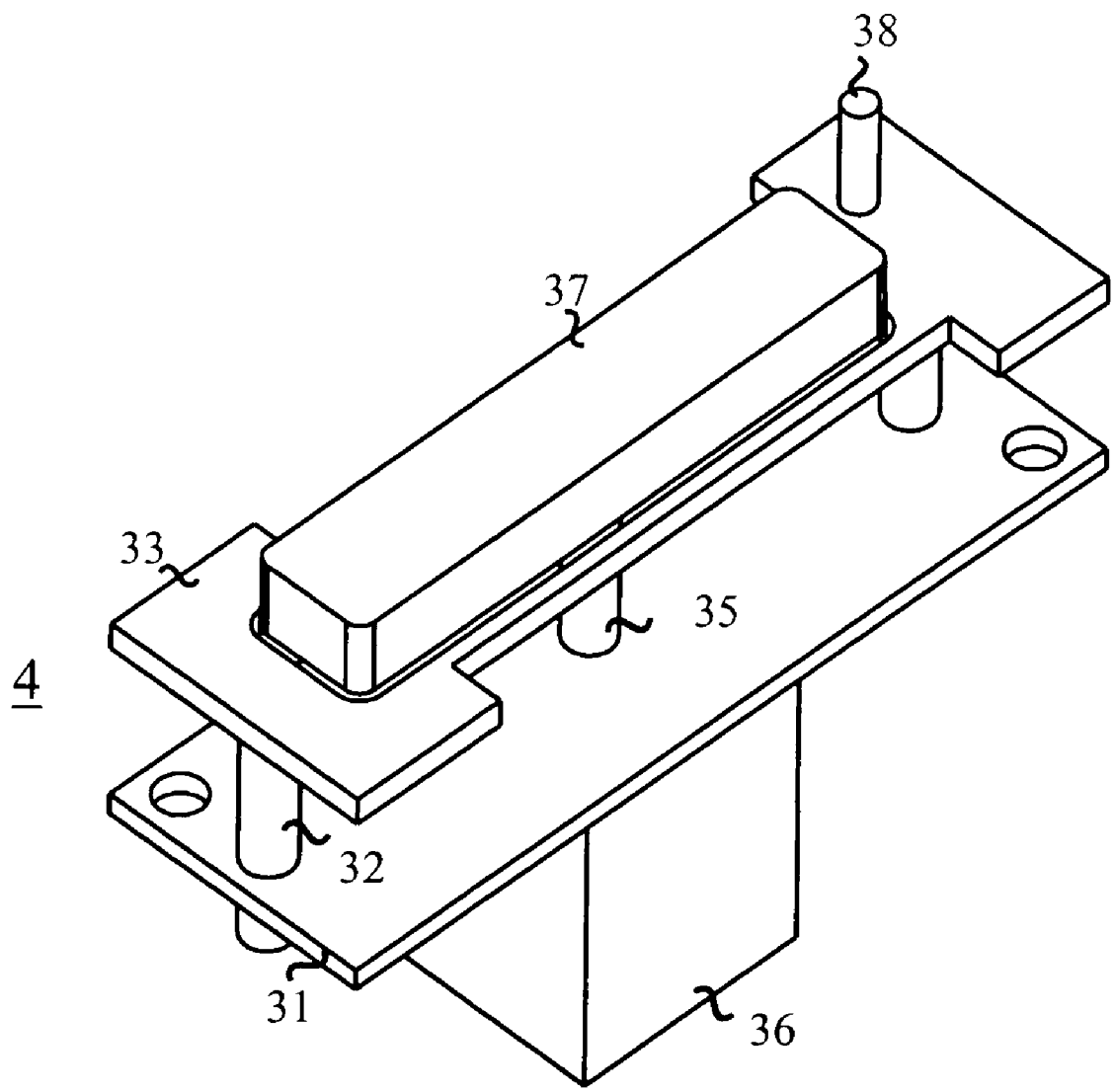
FIG. 4 presents means according to a preferred embodiment of the invention for labeling of the image data receiving means in the cassette tunnel of a mammography apparatus.

The means 3 for the labeling of films presented in FIG. 4 comprises a frame part 31, a carriage 33 functionally connected to the frame part 31 via guide rails 32, a screw conveyor 35 for moving the carriage and a motor 36 driving the screw conveyor. Mounted on the carriage is a display or other recording element 37 and a contact means 38, such as a pin or equivalent. A labeling device 4 like this can be arranged in conjunction with the cassette tunnel either so that the desired markings can be recorded on the film while the cassette is in a typical imaging position or so that the cassette is driven to a given labeling position (LP) for labeling, as shown in FIG. 3. In both cases, the means of the invention for moving the cassette can be utilized for opening and closing the shutter of the labeling window of the cassette so that when the cassette is in its labeling position, its labeling window is located in a position where, as the carriage 33 is being raised, the contact means 38 meets a counterpart provided in the shutter structure of the labeling window of the cassette. Thus, the labeling window of the cassette can be opened and closed by moving the cassette itself by the arrangement of the invention.

The recording means 37 may be e.g. a liquid crystal display, from which the desired data can be projected onto the film in a known manner by using a lamp placed behind the display. When a liquid crystal display is used, it is preferably so disposed in the labeling means structure that the display 37 can be moved as close to the film as possible for the time required for labeling, e.g. by using a vertical motion of the carriage as in the solution presented in FIG. 4. In this case, it may be unnecessary to provide any separate optical devices between the display and the film to ensure a successful labeling exposure, although a suitable lens is generally required. If a film marking technique is used that requires no movement of the display 37 or equivalent element, then the solution presented in FIG. 4 can naturally be further considerably simplified. In this case, an arrangement in which the display 37 or equivalent element is immovably mounted directly on the frame part 31 and in which the contact element 38 used is e.g. a solenoid will be sufficient.

The labeling function can naturally also be made by using previously known solutions based on a scanning technique, in which case the labeling window structure of the cassette does not necessarily comprise an actual shutter that can be opened/closed. In a scanning technique, the essential feature is that a printing or exposure head is moved over the labeling area of the film. When the labeling is implemented utilizing cassette moving means according to the present application, a recording head of this type can be immovably mounted in the cassette tunnel or in its immediate vicinity and the scanning movement can be implemented as a movement of the cassette. Devices based on scanning technique generally use recording heads that expose the film in only one dimension, while another dimension of the marking is accomplished by the scanning movement itself. For example, a single-row LED display is considerably cheaper than a corresponding matrix display.

This naturally also applies to many other techniques, such as optical fibers.

The above-described opening/closing movements of the labeling window will be unnecessary and can be omitted in solutions where a labeling window substantially impermeable to wavelengths of visible light, and a recording element producing information that is capable of penetrating the cassette's labeling window impermeable to visible light, or that can otherwise, e.g. in a converted form, be conveyed through it, are used.

The advantages of the arrangement of the invention are clearly visible in screening studies as mentioned above, in which it can be utilized e.g. as follows: After taking the first image, the operator of the imaging apparatus emerges from behind the radiation shield and steps in front of the apparatus, holding the next cassette ready in his hand, presses the cassette eject switch on that side where he wants the cassette to come out of the cassette tunnel, or removes the cassette automatically ejected by the apparatus and inserts the new cassette via the opening of the cassette tunnel, whereupon the automatic system of the apparatus positions the cassette in the correct position. Next, the C-arm of the device is turned into the next projection angle and, if necessary, the position of the object to be imaged is corrected, and thus the apparatus is ready to take the next image. If the apparatus is additionally provided with means for automatic labeling of the cassette according to a preferred embodiment of the invention before it is driven out of the cassette tunnel, then the imaging work can be carried out considerably more effectively than before as the time spent on supplementary work associated with the imaging process is substantially reduced.

The amount of manual work to be done in connection with the arrangement of the invention can be further reduced by adding to the cassette tunnel feed opening a cassette feed magazine operated by any known technique. The arrangement of the invention can even be thought of as being developed as far as creating a mammography imaging line that is completely automated except for the positioning of the object to be imaged. The first part of such a line could consist of a station for loading cassettes with film, said station either simultaneously functioning as the cassette feed magazine of the mammography apparatus or being connected to a cassette feed magazine via a cassette conveyor line, from which magazine the cassette is fed into the cassette tunnel of the mammography apparatus, where the cassette moving means provided in the tunnel take care of the cassette movements needed for its positioning in connection with imaging, possible cassette motion and labeling during imaging and finally driving the cassette out of the cassette tunnel, either from the same side as or from a different side than where the cassette was inserted into the tunnel, in which case, depending on the solution, the cassette is conveyed either via the same aforementioned cassette conveyor line or via a separate line to a film development unit containing means known in themselves for automatic removal of the film from the cassette and for its development.

Besides facilitating the supplementary functions to be performed in connection with the imaging process, the arrangement of the invention can also be utilized e.g. in so-called stereotactic imaging, which involves taking at least two pictures of the same object on the same film or e.g. on a digital cassette, typically requiring the cassette to be moved to a new position between the exposures. In the arrangement of the invention, the cassette motion can be controlled e.g. by means of pre-input operation parameters or by operating the motor of the driving roller via control buttons on the imaging apparatus.

Furthermore, the arrangement of the invention provides possibilities e.g. for taking film-based narrow-beam tomograms with a mammography apparatus. In this type of imaging, the object to be imaged is scanned with a radiation beam that is narrower than the object to be imaged while the position of the radiation source and film cassette in relation to the stationary tissue layer or area to be imaged is changed during the imaging process, e.g. by revolving the imaging means around the object to be imaged, the film cassette being simultaneously moved in a manner required by the imaging condition known in itself so that the radiation beam also sweeps over the film during the imaging cycle.

Although the prices of digital sensors are continuously falling, especially sensors having a large surface area are still very expensive. The arrangement of the invention makes it possible to use a digital sensor for taking mammographic radiographs e.g. by using a narrow sensor attached to a suitable cassette or plate, moving the sensor in synchronism with the scanning movement of a narrow radiation beam implemented by keeping the radiation source stationary while moving a screen placed near the radiation source to define the radiation beam.

The examples presented above are not meant to be an exhaustive list of concrete and preferred ways of applying the invention; instead, its embodiments may vary within the scope of the inventive idea defined in the following claims.

The invention claimed is:

1. Arrangement for a film cassette image data receiving means for use in mammography, said arrangement comprising:
   a cassette tunnel arranged in a mammographic imaging apparatus, which cassette tunnel includes a space into which the cassette is insertable via at least one feed/eject opening in said cassette tunnel, which said space is so disposed that said space is at least partially located in an imaging area of the mammography apparatus,
   wherein the arrangement comprises means for moving the cassette in the aforesaid cassette tunnel, said means for moving the cassette including means for drawing the cassette into said cassette tunnel and ejecting the cassette out of the cassette tunnel, and wherein said means for moving the cassette further includes control means for moving the cassette to a desired position in said cassette tunnel, and
   wherein the arrangement further comprises means for detecting the entry of the cassette in said cassette tunnel and for transmitting a start signal to said means for moving the cassette.

2. Arrangement as defined in claim 1, wherein said means for moving the cassette comprise means for moving said cassette in opposite directions.

3. Arrangement as defined in claim 2, wherein said means for moving the cassette comprise means for moving said cassette in opposite directions.

4. Arrangement as defined in claim 1, wherein said means for detecting the entry of the cassette in said cassette tunnel comprising a sensor located in said cassette tunnel substantially near said cassette tunnel feed/eject opening.

5. Arrangement as defined in claim 1, wherein said control means comprise means for moving and automatic stopping said means for moving the cassette after the cassette has been fed into said cassette tunnel and moved a desired distance.

6. Arrangement as defined in claim 5, wherein said means for stopping the motion of the cassette comprises at least one sensor arrangement, comprising means for detecting that the cassette has been driven to a certain position in the cassette tunnel and means for issuing a stop signal to said means for moving the cassette.

7. Arrangement as defined in claim 1, wherein said arrangement comprises means for starting said means for moving the cassette to eject said cassette out of the cassette tunnel.

8. Arrangement as defined in claim 7, wherein said means for starting the ejection of the cassette out of the cassette tunnel comprises at least one cassette eject button placed outside said cassette tunnel.

9. Arrangement as defined in claim 1, wherein the size of the cassette tunnel is changeable to accommodate different size cassettes and said means for moving the cassette are so disposed in the cassette tunnel such that the position of said means for moving in said cassette tunnel is changeable so that when said cassette tunnel is changed to suit different size cassettes, the means for moving the cassette can also be moved correspondingly.

10. Arrangement as defined in claim 1, wherein said at least one feed/eject opening is disposed on at least one side of said cassette tunnel.

11. Arrangement as defined in claim 10, wherein said arrangement comprises a sensor system fitted substantially in a vicinity of each of said at least one feed/eject opening, said sensor system comprising means for detecting entry of the cassette in said cassette tunnel and for transmitting a start signal to said means for moving the cassette to draw said cassette into said cassette tunnel.

12. Arrangement as defined in claim 10, wherein said arrangement comprises at least one button for starting an ejection of the cassette from said cassette tunnel, one of said at least one button being placed substantially near each of said at least one feed/eject opening of said cassette tunnel, and said at least one button comprises means for transmitting a control signal to said means for moving the cassette that will cause said means for moving the cassette to drive said cassette out of the cassette tunnel via the feed/eject opening which corresponds to the button from which the control signal to the means for moving the cassette was issued.

13. Arrangement as defined in claim 1, wherein said cassette tunnel is disposed in conjunction with a compression plate, bucky, bottom shelf structure of the mammography apparatus substantially in the area of at least that end of said arrangement which comes into contact with a chest of a patient.

14. Arrangement as defined in claim 1, wherein said means for moving the cassette comprise at least one driving roller element, which comes into contact with the cassette.

15. Arrangement as defined in claim 14, wherein said at least one driving roller element is functionally connected to a drive motor via a turning shaft.

16. Arrangement as defined in claim 15, wherein said at least one driving roller is movably mounted on a wall structure delimiting said cassette tunnel so that the turning shaft of said at least one roller goes through said wall structure via an elongated aperture provided therein, said elongated aperture forming a passage for said means for moving the cassette to allow said means for moving the cassette to be moved to a new position when a size of the cassette tunnel is changed.

17. Arrangement as defined in claim 16, wherein said means for moving the cassette are mounted on a carriage which is arranged to be movable along a guide rail substantially parallel to said elongated aperture and which is connected via a draw strip to a spring tending to draw the carriage toward a side of the cassette tunnel which contacts a chest of a patient during imaging.

18. Arrangement as defined in claim 14, wherein said at least one driving roller element is disposed substantially on a side opposite to that end of said cassette tunnel which comes into contact with a chest of a patient during imaging.

19. Arrangement as defined in claim 14, wherein said at least one driving roller element is disposed substantially at a middle of the cassette tunnel.

20. Arrangement as defined in claim 1, wherein said arrangement comprises means for exposing, printing or by a corresponding method recording patient information and imaging parameters and other similar data on a film via a labeling window disposed in the cassette, said means being fitted in said cassette tunnel.

21. Arrangement as defined in claim 20, wherein said control means comprise means for driving the cassette for labeling after imaging.

22. Arrangement as defined in claim 20, wherein the labeling means comprise a printing, exposure or corresponding means for making a marking containing desired information on the film, said means being either a recording means producing a two-dimensional marking and comprising a display or a narrow recording element.

23. Arrangement as defined in claim 20, wherein said labeling means further comprises a contact element which is arranged to be moved in relation to the cassette so that said contact element meets a counterpart placed in the labeling window structure.

24. Arrangement as defined in claim 20, wherein said control system comprises means for operating said labeling means so that the movements required for performing labeling by a scanning technique are arranged to be implemented by moving the cassette in the cassette tunnel by said means for moving the cassette.

25. Arrangement as defined in claim 24, wherein said control means comprise means for automatic labeling of the cassette after imaging, the control being implemented using means for controlling the cassette movement to drive the cassette for labeling after imaging, means for controlling the motion of the contact element to open and close the labeling window of the cassette, and means for controlling the recording means to perform labeling and means for controlling the motion of the cassette to eject the cassette from said cassette tunnel.

26. Arrangement as defined in claim 1, wherein said control means comprises means for storing and executing at least one predefined sequence of moving the cassette, imaging and labeling.

27. Arrangement as defined in claim 26, wherein said arrangement comprises means for integrating said sequence with other means used in the mammography apparatus, said other means used in the mammography apparatus being selected from the group consisting of means for turning the C-arm, and means for adjusting the height position of the cassette tunnel in relation to an object to be imaged, in which case said sequence may comprise the required movements to make possible taking stereotactic and tomographic images of a predetermined kind.

28. Arrangement as defined in claim 26, wherein at least one command for controlling the operation of the mammography apparatus is arranged to be stored in said control system, said command being selected from the group consisting of:

- detecting the cassette entered into the cassette tunnel,
- driving the cassette into an imaging position,
- performing at least one imaging of the object to be imaged selected from a group consisting of:
  - as a single radiograph;
  - as a magnified image by adjusting the position of the object to be imaged in relation to the cassette so as to produce a desired distance between them;
  - as at least two radiographs by moving the cassette in its feed/eject direction between radiation exposures, and likewise the screen if necessary;
  - as a combination of any two of the preceding alternatives; and
  - as a segmental image by moving the cassette and the radiation source during the radiation exposure;
- moving the cassette into labeling position and open a labeling shutter of cassette,
- printing/projecting patient information and imaging parameters onto film, and
- ejecting the cassette out of the cassette tunnel.

29. Mammography apparatus comprising:
a frame part,
a C-arm connected to said frame part,
a source of an energy form used in the imaging of tissue placed substantially at one end of said C-arm,
means for receiving the form of energy obtained from the source and carrying image information concerning the tissue being imaged,
means for positioning the tissue to be imaged and, if necessary, for compressing the tissue to form a thinner layer situated in an imaging area substantially in the region between said source of an energy form and the receiving means,
said apparatus further comprising a cassette tunnel for a cassette which includes the means for receiving the energy carrying image information, said cassette arranged to be replaceably insertable into the cassette tunnel,
wherein the apparatus further comprises a space in the cassette tunnel for receiving said cassette, said space being at least partially located in the imaging area of the mammography apparatus, and means for moving said cassette in said cassette tunnel by drawing said cassette into said cassette tunnel, moving said cassette in said cassette tunnel to a desired position and ejecting said cassette from said cassette tunnel, and
wherein the arrangement further comprises means for detecting the entry of the cassette in said cassette tunnel and for transmitting a start signal to said means for moving the cassette.

30. A method for moving a cassette which includes an image data receiving means used in mammography apparatus comprising the steps of:
arranging the cassette in a cassette tunnel into a space which is at least partially located in an imaging area of said mammography apparatus;
detecting the entry of the cassette in said cassette tunnel by detecting means and transmitting a start signal to moving means; and
moving said cassette by said moving means, wherein said moving means seizes and drives said cassette into a desired position in said cassette tunnel and ejects said cassette from said cassette tunnel.

31. A method as defined in claim 30, wherein said means for moving the cassette moves said cassette in opposite directions.

32. A method as defined in claim 30, wherein said step of moving said cassette by moving means further comprises the steps of:
receiving the cassette into the cassette tunnel;
moving the cassette during the imaging process stepwise;
positioning the cassette for labeling the film; and
moving the cassette during the labeling phase and to eject the cassette out of said cassette tunnel.

33. A method as defined in claim 30, wherein said means for moving the cassette is used to drive the cassette between radiation exposures into at least two different imaging positions in the cassette tunnel.

34. A method as defined in claim 30, wherein the position of the cassette in the cassette tunnel is probed by means of at least one sensor arranged in said cassette tunnel.

35. A method as defined in claim 30, wherein the cassette is fed into said cassette tunnel, said cassette entry is detected by said sensor and said means for moving the cassette draws the cassette into said cassette tunnel and to position said cassette into a correct imaging position, said correct imaging position being identified by means of a second sensor for positioning the cassette.

36. A method as defined in claim 30, wherein said means for moving the cassette moves said cassette during the radiation exposure.

37. A method as defined in claim 36, wherein the cassette is moved during scanning imaging of the object to be imaged to produce a tomogram or a transillumination radiograph.

38. A method as defined in claim 30, wherein the cassette is positioned for labeling in the cassette tunnel and a contact element comprised in the labeling means contacts a counterpart comprised in the cassette and said means for moving the cassette are operated to move said counterpart and the desired information is recorded on the film by means of exposure, printing or corresponding devices comprised in the labeling means.

39. A method as defined in claim 30, wherein the cassette is positioned for labeling in the cassette tunnel the desired information is recorded by scanning, said scanning is performed by keeping a narrow recording element comprised in the labeling means stationary and performing a scanning movement by moving the cassette by operating said means for moving the cassette while a shutter which may be used to protect the labeling window of the cassette is brought before the labeling scanning movement into contact with a contact element comprised in the labeling means in order to keep the shutter in place during the labeling scanning movement.

40. A method as defined in claim 30, wherein the cassette is ejected from said cassette tunnel after imaging and labeling, automatically or by using an eject button comprised in the control means of the mammography apparatus.

41. A method as defined in claim 30, wherein the cassette is moved by means of at least one driving roller.

42. A method as defined in claim 30, wherein when the size of the cassette tunnel is changed in a manner to fit a plurality of cassettes, the position of the means for moving said cassette in the cassette tunnel is changed.

43. A method as defined in claim 30, wherein said means for moving the cassette is used as part of a mammographic imaging line in which a first stage is an automatic film loading station for a cassette from where the cassette is fed into the cassette tunnel of the mammography apparatus, in which in the cassette tunnel are situated said means for moving the cassette and the means for its positioning, imaging of tissue to be imaged and labeling of the cassette.

44. Arrangement for image data receiving means for use in mammography, said arrangement comprising:
a space defined within a mammographic imaging apparatus, into which space the image data receiving means is insertable via a feed/eject opening of said space, which is so disposed that the image data receiving means is at least partially located in the imaging area of the mammographic imaging apparatus, wherein the arrangement comprises means for moving the image data receiving means in the aforesaid space, and
wherein the arrangement further comprises means for detecting the entry of the cassette in said cassette tunnel and for transmitting a start signal to said means for moving the cassette.

* * * * *